(12) United States Patent
Boyles et al.

(10) Patent No.: US 10,221,117 B2
(45) Date of Patent: Mar. 5, 2019

(54) POLYCARBONATES HAVING SUPERIOR DIELECTRIC PROPERTIES SUITABLE FOR ENERGY DENSE CAPACITORS

(71) Applicant: SOUTH DAKOTA BOARD OF REGENTS, Pierre, SD (US)

(72) Inventors: David A. Boyles, Rapid City, SD (US); John T. Bendler, Rapid City, SD (US); Tsvetanka Filipova, Rapid City, SD (US)

(73) Assignee: South Dakota Board of Regents, Pierre, SD (US)

( * ) Notice: Subject to any disclaimer, the term of this patent is extended or adjusted under 35 U.S.C. 154(b) by 31 days.

(21) Appl. No.: 15/683,890

(22) Filed: Aug. 23, 2017

(65) Prior Publication Data

US 2017/0369409 A1    Dec. 28, 2017

Related U.S. Application Data

(63) Continuation of application No. PCT/US2015/017300, filed on Feb. 24, 2015.

(51) Int. Cl.
| | |
|---|---|
| *C08G 63/02* | (2006.01) |
| *C07C 39/367* | (2006.01) |
| *C07C 39/42* | (2006.01) |
| *C08G 64/10* | (2006.01) |
| *H01B 3/42* | (2006.01) |
| *H01G 4/18* | (2006.01) |
| *C07C 43/295* | (2006.01) |
| *H01G 4/32* | (2006.01) |

(52) U.S. Cl.
CPC ............ *C07C 39/367* (2013.01); *C07C 39/42* (2013.01); *C07C 43/295* (2013.01); *C08G 64/10* (2013.01); *H01B 3/426* (2013.01); *H01G 4/18* (2013.01); *H01G 4/186* (2013.01); *C07C 2601/02* (2017.05); *C07C 2601/04* (2017.05); *C07C 2601/08* (2017.05); *C07C 2601/14* (2017.05); *C07C 2601/16* (2017.05); *H01G 4/32* (2013.01)

(58) Field of Classification Search
USPC .................. 528/219, 271, 272, 273, 274
See application file for complete search history.

(56) References Cited

U.S. PATENT DOCUMENTS

| | | | |
|---|---|---|---|
| 3,062,781 A | 11/1962 | Bottenbruch | |
| 4,533,690 A | 8/1985 | Rosenquist | |
| 4,745,215 A | 5/1988 | Cox et al. | |
| 5,155,205 A | 10/1992 | Ebert et al. | |
| 5,232,804 A | 8/1993 | Molaire | |
| 5,357,033 A | 10/1994 | Bendler et al. | |
| 5,486,577 A | 1/1996 | Farah et al. | |
| 5,532,331 A | 7/1996 | Bales et al. | |
| 6,303,733 B1 | 10/2001 | Lau et al. | |
| 6,630,520 B1 | 10/2003 | Bruza et al. | |
| 7,125,951 B2 | 10/2006 | Boyles et al. | |
| 7,642,335 B2 | 1/2010 | Scindia et al. | |
| 7,687,584 B2 | 3/2010 | Boyles et al. | |
| 8,218,291 B2 | 7/2012 | Silvi et al. | |
| 8,247,484 B2 | 8/2012 | Tan et al. | |
| 8,487,050 B2 | 7/2013 | Omote et al. | |
| 2009/0312474 A1 | 12/2009 | Tan et al. | |
| 2010/0067172 A1 | 3/2010 | Zhang et al. | |
| 2011/0105686 A1 | 5/2011 | Kashiwagi | |
| 2012/0082833 A1 | 4/2012 | Shafer | |
| 2013/0035441 A1 | 2/2013 | de Brouwer et al. | |
| 2014/0226256 A1 | 8/2014 | Ichikawa et al. | |

FOREIGN PATENT DOCUMENTS

| | | |
|---|---|---|
| CN | 103102665 A | 5/2013 |
| EP | 0406640 A2 | 6/1990 |
| EP | 1947131 A1 | 7/2008 |
| GB | 965085 | 7/1964 |
| JP | 10310692 A | 11/1998 |
| JP | 2011148940 A | 8/2011 |
| WO | 9003407 A1 | 4/1990 |
| WO | 9109081 A1 | 6/1991 |

OTHER PUBLICATIONS

Bendler, John T., et al., "Dielectric Properties of Bisphenol A Polycarbonate and Its Tethered Nitrile Analogue", Macromolecules, 2013, vol. 46, pp. 4024-4033. May 13, 2013.

Bendler, J.T. et al., "Electrical Properties of a Novel Fluorinated Polycarbonate", European Polymer Journal, vol. 48 (2012) pp. 830-840. Feb. 10, 2012.

Fontanella, J. J. et al., "Dielectric Studies of Tetraaryl and Triaryl Polycarbonates and Comparisons with Bisphenol A-Polycarbonate", Journal of Polymer Science Part B: Polymer Physics 2012, vol. 50, pp. 289-304. Nov. 15, 2011.

European Patent Office, "Written Opinion of the International Searching Authority", filed in connection to PCT/US2015/017300, dated Oct. 29, 2015.

*Primary Examiner* — Terressa Boykin (74) *Attorney, Agent, or Firm* — McKee, Voorhees & Sease, PLC (57) ABSTRACT

The present invention provides monomers, analogs, and/or derivatives of bisphenols substituted with one or more fluoromethyl groups. These monomers, analogs, and/or derivatives can be used to form oligomers and/or polymers, which in turn can be used to make compounds with dielectric properties suitable for dielectric materials, including for example, use in energy dense capacitors. In a preferred embodiment, the compounds can comprise a polycarbonate of a homopolymer, copolymer, and/or terpolymer of a bisphenol with one or more fluoromethyl substitution groups. In an aspect of the invention the compounds chosen can be selected based on various desired characteristics, including, for example, their energy density, glass transition temperature, dielectric loss, and/or dipole density.

20 Claims, 3 Drawing Sheets

POLYCARBONATES HAVING SUPERIOR DIELECTRIC PROPERTIES SUITABLE FOR ENERGY DENSE CAPACITORS

CROSS REFERENCE TO RELATED APPLICATION

This application is a continuation of PCT/US2015/017300, filed Feb. 24, 2015, which is herein incorporated by reference in its entirety.

FIELD OF THE INVENTION

The invention relates to novel monomers. The monomers are derived from bisphenols with fluoromethyl substitutions. The monomers can be used to form compounds with dielectric properties suitable for dielectric materials, including for example, use in energy dense capacitors. In particular the materials include polycarbonate homopolymers, copolymers, and/or terpolymers of bisphenols with fluoromethyl substitutions.

BACKGROUND OF THE INVENTION

Dielectric materials have high polarizability and are able to store electrostatic energy through charge separation of electric charges of opposite sign. Typically, capacitors are composed of metal electrodes or plates that are separated by a layer of dielectric material. An applied potential difference is used to 'charge' the capacitor by transferring electric charge from one electrode to the other. High voltage capacitors typically exist in cylindrical sandwiching of dielectric material and metal foil electrode. The dielectric material must be capable of holding an electric field across the electrodes without discharging it. When the electrical field within a dielectric medium changes, the momentary delay in change of the dielectric permittivity is referred to as the dielectric relaxation.

Commonly, dielectric materials have included inorganics such as mica and ceramics, although these materials suffer from brittleness and other insufficiencies. As a consequence, the use of polymeric materials has been explored, including high-polymer films such as polypropylene, polycarbonates, and polyimides. Enticing properties of such compounds include, for example, transparency, ductility, and low weight. Further polycarbonates are amorphous, glassy, non-crystalline materials ideally suited to film formation necessary for wound film capacitors. However, these materials often suffer from low glass transition temperatures making them impractical for many applications. Additionally, each type of material is limited by the temperatures at which it is able to sustain its breakdown voltage, inherent ability to be processed, and inherent dielectric permittivity. Commercial polycarbonate (BPA-PC) itself has been utilized many years in capacitors; however, it is desirable to develop polycarbonates with superior dielectric properties for use in energy dense capacitors. The use of polymeric materials with substitutions to the polymer backbone has been explored. For example, bis[4'-(3-fluoro-4-hydroxyphenyl)-phenyl]propane (DiF TABPA) has fluorine substituted onto the benzene rings located within the polymer backbone. See Bendler et al., *Electrical Properties of a Novel Fluorinated Polycarbonate*, 48 EURO. POLYMER J. 830-840 (2012). However, such compounds were found to either lack sufficient dielectric permittivity or to suffer from dielectric loss at temperatures that were too high, i.e., the loss would occur to close to room temperature. Substitutions of tethered nitrile groups onto the polymer backbone have also been explored. For example, 4,4-bis(4-hydroxyphenyl)pentanenitrile homopolycarbonate (CN-PC) was prepared and tested. See Bendler et al., *Dielectric Properties of Bisphenol A Polycarbonate and Its Tethered Nitrile Analogue*, 46 MACROMOLECULES 4024-4033 (2013). It was found that tethered nitrile groups created an encumbrance in rotation, which prevented adequate dipole rotation. Further, it was found that the nitrile substitutions were unable to exert the calculated effect of their dipoles, owing to restricted rotation on account of their size. Additionally, losses were into the working range of the capacitor.

Accordingly, it is an objective of the claimed invention to develop monomeric bisphenols containing one or more fluoromethyl groups in order to enhance the compounds dielectric constant.

A further object of this invention is to develop compounds having enhanced dielectric constants and low temperature dielectric losses suitable for pulsed power and other capacitors.

Still a further object of this invention is to dielectric materials, including, for example capacitors, comprising polycarbonates of homopolymers, copolymers, terpolymers, analogs, and/or other derivatives of bisphenols substituted with one or more fluoromethyl group; wherein such dielectric materials possess enhanced dielectric properties.

BRIEF SUMMARY OF THE INVENTION

The present invention provides monomers based on and/or derived from bisphenols with fluoromethyl substitutions. The monomers can be used to form compounds with dielectric properties suitable for dielectric materials, including for example, use in energy dense capacitors. In an aspect of the invention the compounds chosen can be selected based on various desired characteristics, including, for example, their energy density, glass transition temperature, dielectric loss, and/or dipole density.

In an embodiment, the present invention comprises a polycarbonate of a homopolymer, copolymer, and/or terpolymer of a bisphenol with one or more fluoromethyl substitution groups. The polycarbonate can comprise a monomer, analog, and/or derivative of the following structure where n is between 1 and 1000; wherein $R_1$ or $R_2$ are substitutions of the formula $C_xH_yF_z$ where x can be any number from 1 to 5, y can be any number from 1 to 8, and z can be any number from 1 to 3, and at least either $R_1$ or $R_2$ is fluorinated.

In a further embodiment of the invention, the polycarbonate of a homopolymer, copolymer, and/or terpolymer of a bisphenol with one or more fluoromethyl substitution groups has enhanced dielectric properties.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to monomers based on and/or derived from bisphenols with one or more fluoromethyl substitutions. The monomers can form compounds with dielectric properties suitable for dielectric materials, including for example, use in energy dense capacitors. In particular the materials include polycarbonate homopolymers, copolymers, and/or terpolymers of bisphenols with fluoromethyl substitutions. The compounds of the invention have many advantages over existing dielectric materials, including, for example, high glass transition temperatures, greater dielectric permittivity, and a low gamma intensity maximum. Additionally the compounds of the invention possess fast relaxations of the fluoromethyl groups which represent a loss that contributes to high electric constants when compared to existing polycarbonates.

The embodiments of this invention are not limited to particular use for dielectric materials, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range (e.g., 1 to 5 includes 1, 1.5, 2, 2.75, 3, 3.80, 4, and 5).

Definitions

So that the present invention is more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "analog" means a molecular derivative of a molecule. The term is synonymous with the terms "structural analog" or "chemical analog."

As used herein, the term "capacitance" is expressed by the equation C as a function of voltage=dQ/dV where C is capacitance measured in farads, Q is the quantity in coulombs, and V is the applied voltage in volts. Depending upon its magnitude, capacitance can be expressed in farads, microfarads, or picofarads.

As used herein "dielectric permittivity (ε)" is an expression of the absolute dielectric properties of a material or medium. The dielectric permittivity is directly proportional to capacitance C, and is defined according to the equation C=ε/1, wherein A is the area of the electrodes and 1 is the distance between them. In combination with the definition C=dQ/dV given earlier, this equation indicates that the greater the permittivity ε, the greater the charge that can be stored on the electrodes for a given potential difference. The dielectric permittivity is also expressed as the differential coefficient of rate of change of the displacement field D, the external charges applied to the electrodes of the capacitor, with the electric intensity E, the macroscopic force field averaged over the dielectric medium, or ε=dD/dE, in units of coulomb/per volt-meter, or farad per meter.

As used herein the term "dipole moment (μ)" refers to an asymmetric charge distribution inside a neutral molecule. The dipole moment is considered to be the product of the magnitude of the charges multiplied by the distance of separation between the charges. Dipole moment is measured in units of debye.

As used herein, the term "oligomer" refers to a molecular complex comprised of between one and ten monomeric units. For example, dimers, trimers, and tetramers, are considered oligomers. Furthermore, unless otherwise specifically limited, the term "oligomer" shall include all possible isomeric configurations of the molecule, including, but are not limited to isotactic, syndiotactic and random symmetries, and combinations thereof. Furthermore, unless otherwise specifically limited, the term "oligomer" shall include all possible geometrical configurations of the molecule.

As used herein the term "polarizability (α)" refers to a measure of the ability of a molecule or substituent group exposed to an electric field to develop a dipole moment μ along the direction of the field, by displacement of its electrons relative to the nuclear framework, and through partial alignment of any permanent dipole moments present. The total polarization P of a dielectric material is the molecular number density n times the dipole moment µ. Three types of responses within the dielectric material contribute to the polarization P of a dielectric material. They are first, the electronic polarizability $\alpha_e$, or the dipole moment resulting from the induced displacement under the local electric field of the negative electrons relative to the positively charged atomic nuclei. The second is the orientation polarizability $a_\mu$, resulting from the partial alignment of the permanent bond dipoles along the local electric field. The third is the distortion polarizability $\alpha_d$ resulting from the bending and stretching of the chemical bonds within the molecules that tie together atoms bearing different formal charges, owing to their different electronegativities.

As used herein the term "polymer" refers to a molecular complex comprised of a more than ten monomeric units and generally includes, but is not limited to, homopolymers, copolymers, such as for example, block, graft, random and alternating copolymers, terpolymers, and higher "x"mers, further including their analogs, derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

As used herein the term "relative permittivity" or "dielectric constant k" refers to the ratio of the permittivity c of a dielectric material to that $\varepsilon_0$ of a vacuum, or $k=\varepsilon/\varepsilon_0$, wherein $\varepsilon_0$ is $8.85 \times 10^{-12}$ farad per meter. The permittivity of some dielectric materials decreases with increasing field strength. Typically, the dielectric permittivity decreases as the frequency of the applied energy is increased.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Monomers, Analogs, and Derivatives of Bisphenols with Fluoromethyl Substitution

The present invention comprises a bisphenol monomer as shown in Structure I and/or its analogs and derivatives:

Structure I $R_1$ and $R_2$ can be substitutions of the formula $C_xH_yF_z$ where x can be any number from 1 to 5, y can be any number from 1 to 8, and z can be any number from 1 to 3 and n can be any number from 1 to 1,000 and the average molecular weight is no greater than 250,000 Da. Additionally, $R_1$ and $R_2$ can be symmetrical or asymmetrical and may or may not form cyclic structures between their respective substitutions. When forming monomers, analogs, and/or other derivatives of bisphenols one can balance the mass of the monomers with the number of rotatable fluoromethyl dipole groups, to control the dipole density of the molecule. This is because an increase in mass can reduce the dipole density of the monomer.

Preferred bisphenol compounds containing fluoromethyl groups for preparing the polycarbonates of the invention, include, but are not limited to:

G.

H.

The monomers, analogs, and/or derivatives of the invention can be used in any desired applications and/or compositions. For example, the monomers, their analogs and derivatives can form polymers, including, homopolymers, copolymers, terpolymers, analogs, and/or derivatives. Those polymers can include, but are not limited to, resins, epoxy resins, polycarbonates, polyacrylates, polyesters, polyethers, polysiloxanes, polysulfides, polysulfones, and/or any other polymers, copolymers, and/or terpolymers that can be synthesized from monomers of the invention.

In a preferred embodiment, the monomers, analogs, and/or derivatives are used to form polymers in polycarbonates. Such polycarbonates can be homopolymers, copolymers, or terpolymers, as well as analogs and other derivatives of the above bisphenols in the form of homopolymers, of mixtures of the above in the form of copolymers, or of the above polymerized with other bisphenols, including bisphenol A, TABPA, or other bisphenols. For example, the polycarbonates can be homopolymers, copolymers, terpolymers, analogs, and/or derivatives of Structure II Structure II where $R_1$ and $R_2$ can be substitutions of the formula $C_xH_yF_z$ where x can be any number from 1 to 5, y can be any number from 1 to 8, and z can be any number from 1 to 3 and n can be any number from 1 to 1,000 and the average molecular weight is no greater than 250,000 Da. Additionally, $R_1$ and $R_2$ can be symmetrical or asymmetrical and may or may not form cyclic structures between their respective substitutions.

The polymer backbone is the combination of monomeric units used to form the homopolymers, copolymers, terpolymers, analogs, and/or other derivatives of bisphenols together, except for the substitutions at $R_1$ and $R_2$ as shown in Structure I. By selecting different homopolymers, copolymers, terpolymers, analogs, and/or other derivatives of the polycarbonate of a bisphenol, one can tailor various attributes of the compounds. For example, by increasing the number of rings on the polymer backbone, one can increase the glass transition temperature thereby making the material of the present invention workable at higher temperatures and suitable for applications functioning at higher temperatures. Thus, monomers providing desired dielectric properties can be copolymerized with polymers having high glass transition temperatures, such as high tetraaryl materials.

Additionally, other polymer units can be added to any of the homopolymers, copolymers, terpolymers, and/or derivatives of bisphenol to form polymeric polycarbonates based on bisphenol. The various polymer backbones may be substituted to include one or more halogens, nitrile groups, nitrogen dioxide groups, or other groups.

Preferably the aforementioned bisphenol compounds can be copolymers of bisphenol A, tribisphenol A (TriBPA), tetraarylbisphenol A (TABPA), and 4,4'-bisphenol (DOD). Thus, in preferred embodiments of the invention, the polycarbonate copolymers of the present invention may comprise, but are not limited to, TABPA/BPA-PC, TABPA/DOD-PC, TriBPA/BPA-PC, TriBPA/DOD-PC, and DOD/BPA-PC with one or more fluoromethyl substitutions. For a polycarbonate with two monomeric units, the mole fraction of each monomeric unit may vary from about 0.001 to about 0.999, from about 0.01 to about 0.99, from about 0.05 to about 0.95, from about 0.10 to about 0.90, from about 0.20 to about 0.80, from about 0.3 to about 0.7, or from about 0.4 to about 0.6. For a terpolycarbonate, a copolycarbonate with three monomeric units, each monomeric unit may have a mole fraction of from about 0.001 to about 0.999, from about 0.01 to about 0.99, from about 0.05 to about 0.95, from about 0.10 to about 0.90, from about 0.20 to about 0.80, from about 0.3 to about 0.7, or from about 0.4 to about 0.6. The total of the all mole fractions of all monomeric units in a copolycarbonate equals 1.

The molecular weight of the polycarbonate, either a homopolymer or copolymer, may vary from about 1,000 to about 250,000 Da, to about 200,000 Da, or to about 150,000 Da; from about 2,000 to about 250,000 Da, to about 200,000 Da, or to about 150,000 Da; from about 5,000 to about 250,000 Da, to about 200,000 Da, or to about 150,000 Da; from about 10,000 to about 250,000 Da, to about 200,000 Da, or to about 150,000 Da; from about 25,000 to about 250,000 Da, to about 200,000 Da, or to about 150,000 Da; or from about 50,000 to about 250,000 Da, to about 200,000 Da, or to about 150,000 Da.

The polycarbonate may have a molecular weight distribution of no greater than about 5, no greater than about 4, or no greater than about 3.

The polycarbonate polymers used in the present invention are not limited by commercial sources or methods of preparation. These polycarbonate polymers may readily prepared according to known procedures by reacting a dihydroxyaromatic compound with a carbonate precursor such as phosgene, a haloformate or a carbonate ester, a molecular weight regulator, an acid acceptor and a catalyst. Methods for preparing polycarbonates are known in the art, including interfacial polymerization and melt polymerization.

The molecules of the present invention store energy in the dipole rotation of the present invention as shown below.

For example, in the following structure the rotation is around the C—CF bond.

The molecules orient in an applied electric field to align with the field, thus storing energy, and relax exceptionally rapidly when the field is removed, releasing the stored energy quickly and with low loss. The amount of energy stored is based in part on the dipole density of the molecule. The dipole density is a measurement of the dielectric permittivity divided by the molecules mass and varies in the present invention according to the number fluoromethyl groups present. Thus, by increasing the mass of the molecule the dipole density can be lowered, while other attributes, such as glass transition temperature may be increased. The desired glass transition temperature may be dictated by the end-use desired. Thus, for some uses the glass transition temperature desired may be as high as greater than 180° C. or even greater than 200° C. Generally, the glass transition temperature is preferably at least 120° C., more preferably at least 140° C., even more preferably at least 150° C.

Various molecules were tested to evaluate the imaginary part of relative permittivity versus temperature at a range of frequencies between 10 Hz and 100,000 Hz. Exemplary results for three molecules tested are shown in FIGS. 1-3.

Figure 1:
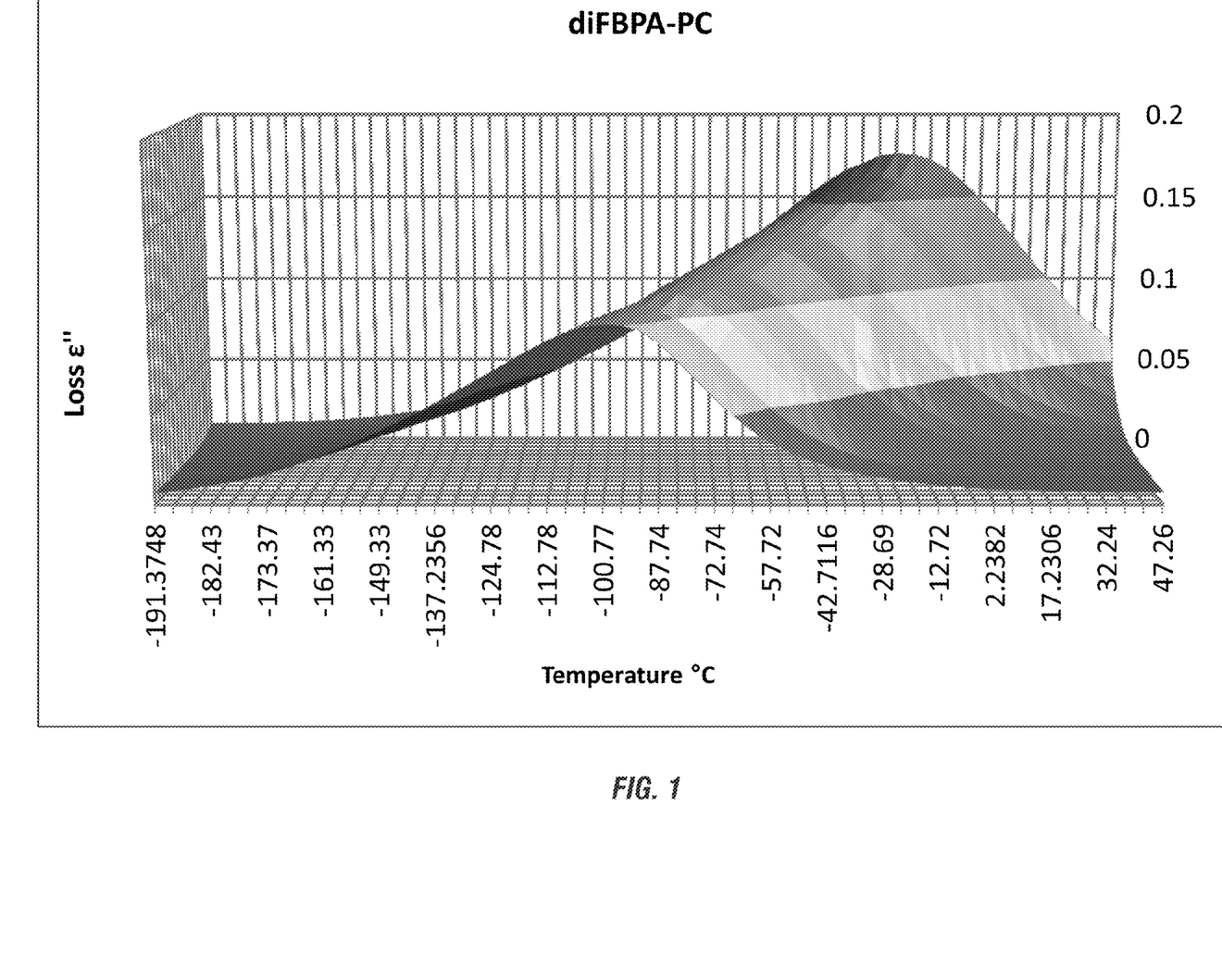
FIG. 1 shows a three-dimensional graph of the imaginary part of relative permittivity versus temperature in Celsius at a range of frequencies for diFBPA-PC. For the frequency of 10 Hz, the peak occurs at −101° C., whereas at 100,000 Hz, the peak occurs at −18° C.

FIG. 1 shows a three-dimensional graph of the imaginary part of relative permittivity versus temperature in Celsius at a range of frequencies for diFBPA-PC, an exemplary composition of the invention. For the frequency of 10 Hz, the peak occurs at −101° C., whereas at 100,000 Hz, the peak occurs at −18° C.

Figure 2:
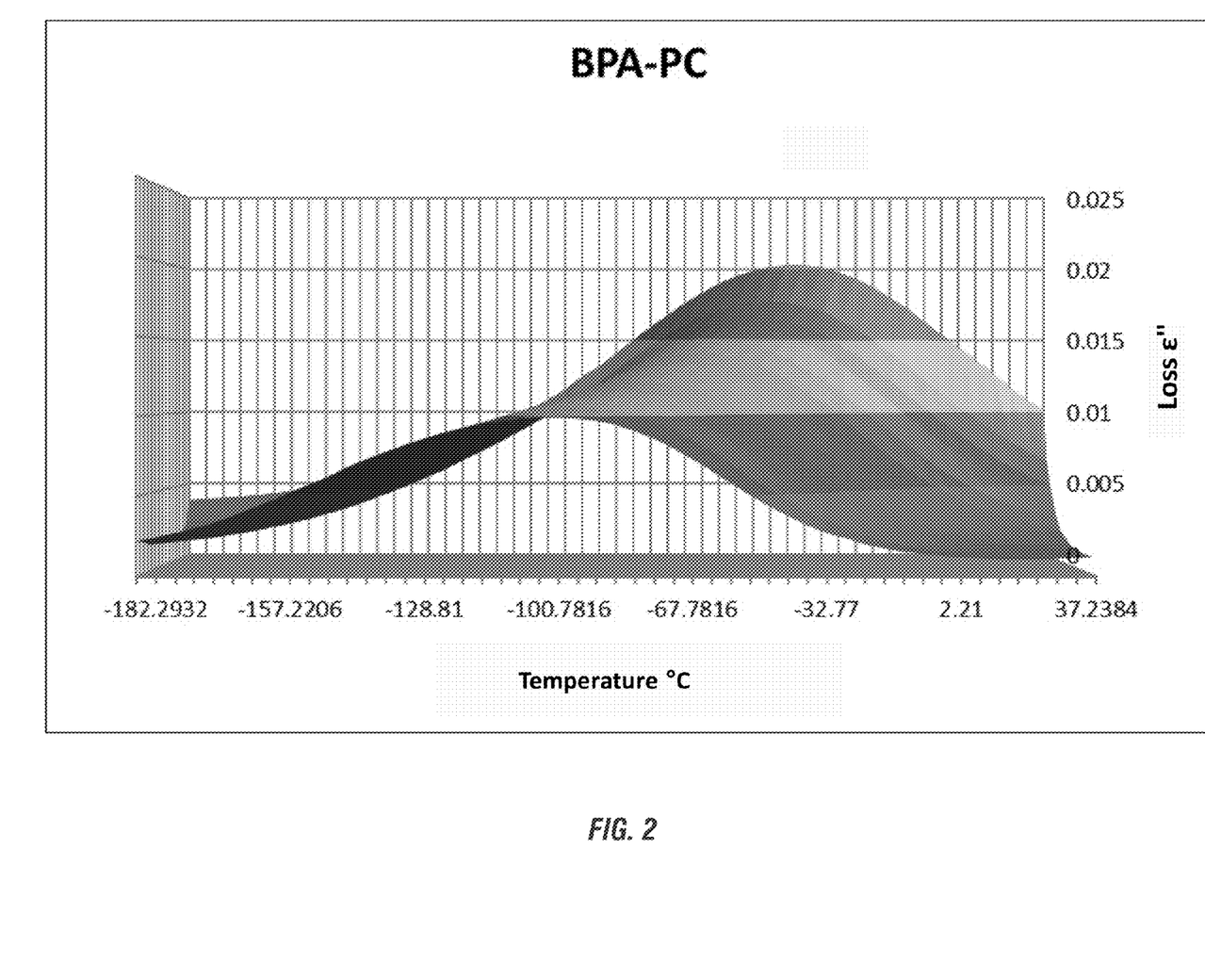
FIG. 2 shows a three-dimensional graph of the imaginary part of relative permittivity versus temperature in Celsius at a range of frequencies for BPA-PC. For the frequency of 10 Hz, the peak occurs at −100° C., whereas at 100,000 Hz, the peak occurs at −38° C.

Similarly, FIG. 2 shows a three-dimensional graph of the imaginary part of relative permittivity versus temperature in Celsius at a range of frequencies for BPA-PC. For the frequency of 10 Hz, the peak occurs at −100° C., whereas at 100,000 Hz, the peak occurs at −38° C.

Figure 3:
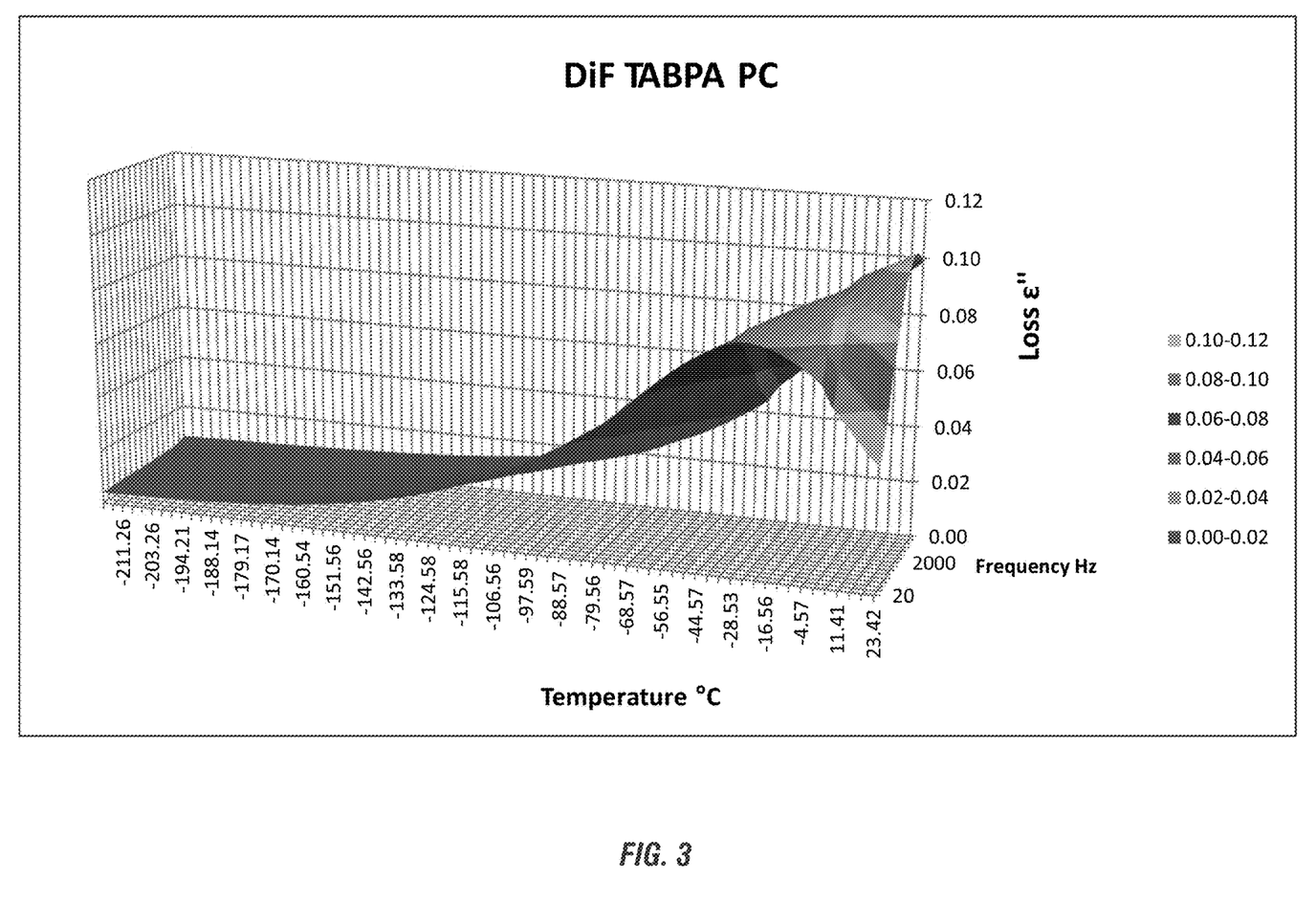
FIG. 3 shows a three-dimensional graph of the imaginary part of relative permittivity versus temperature in Celsius at a range of frequencies for diF TABPA-PC. For the frequency of 10 Hz, the peak occurs at −28° C., whereas at 100,000 Hz, the peak occurs at was outside of the measurable range.

FIG. 3 shows a three-dimensional graph of the imaginary part of relative permittivity versus temperature in Celsius at a range of frequencies for diF TABPA-PC. For the frequency of 10 Hz, the peak occurs at −28° C., whereas at 100,000 Hz, the peak occurs at outside of the measurable range.

As can be seen from this data, the compositions of the invention provide better dielectric properties than those with nitrile substitutions or fluorine substitutions on the benzene rings.

In an aspect of the invention, the fluorinated polycarbonates of the present invention have a high dipole density, thus providing the dielectric material the ability to store energy more effectively and having a high energy density. For example, this allows for the storage of more voltage on a capacitor of a small volume. Preferably the dipole density is between 1 and 8 fluoromethyl groups per polymeric repeat unit, more preferably between 2 and 6 fluoromethyl groups per polymeric repeat unit.

In an aspect of the invention, the fluorinated polycarbonates of the present invention have increased gamma intensity maxima at low temperatures. Having high gamma intensity maxima at a low temperature allows the dielectric material to store energy more effectively. For example, this allows for the storage of more voltage on a capacitor of a small volume. Preferably the gamma intensity maxima occurs at temperatures lower than −30° C., more preferably lower than −50° C., and most preferably lower than −75° C. In another aspect of the invention, loss in the working temperature end frequency range of the capacitor is 0.05 or less, more preferably 0.04 or less, even more preferably 0.03 or less, and most preferably 0.02 or less.

Other factors such as rotation resistance or encumbrance can affect the adequacy of the molecule to provide desired energy storage. For example, the long-tethered nitrile of 4,4-bis(4-hydroxyphenyl)pentanenitrile homopolycarbonate was found to create an encumbrance in rotation, thereby reducing the energy released during relaxation. Further, it was found that a short-tethered nitrile substituted polycarbonate of bisphenol A shown below suffered from too much loss in energy during relaxation.

While not wishing to be bound by the theory, it is believed the energy loss was due to rotational resistance derived from the nitrile group. Thus, it was determined that nitrile substitutions moved the gamma relaxation process too far into the temperature range of the working capacitor and were restricted in size, thus unable to exert their full dipolar effect.

Methods of Preparing the Fluoromethyl Compounds

The fluoromethyl monomers of the present invention may be synthesized through a variety of processes and combination of processes. One example of a synthesis strategy that may be used to make fluoromethyl monomers of the present invention utilizes an acid catalyzed condensation reaction followed by a substitution reaction. For example, condensation of an appropriate ketone with formaldehyde, formalin, paraformaldehyde, or other formaldehyde equivalent to afford a hydroxymethylated ketone derivative followed by direct fluorine substitution using available fluorinating reagents. Alternatively, the hydroxymethylated ketone derivative may be derivatized to a mesylate, triflate, tosylate, or the like and then substituted using an available fluorinating reagent. The resulting fluoromethylated ketones can then be condensed with phenol by known methods to provide the respective bisphenol monomers, which can then be utilized in any composition.

The monomers, analogs, and/or derivatives of Structure I of the present invention may be used to make oligomers and polymers. The polymers can include homopolymers, copolymers, terpolymers, block polymers, polymer blends, combinations and mixtures thereof, and other variations that contain at least one of the monomer units of the present invention. For example, the monomers may be polymerized by interfacial or other known polymerization methods to their corresponding polycarbonates using phosgene, triphosgene, diphenylcarbonate, or other phosgene equivalent. Additionally, the monomers, analogs, and/or derivatives of Structure I of the present invention may be further chemically modified to make derivatives, such as precursors to dielectric materials, other polymers, resins, film, and related products.

Dielectric Materials

While an understanding of the mechanism is not necessary to practice the present invention and while the present invention is not limited to any particular mechanism of action, it is contemplated that, in some embodiments, the monomers, analogs, and/or derivatives of bisphenols with fluoromethyl substitution compounds can be used to form polycarbonates, which can be used for dielectric materials in a capacitor, transformer, or other apparatus employing a dielectric material. In a preferred embodiment, the dielectric material is used in a capacitor including, but not limited to dielectric capacitors, variable capacitors, film capacitors (including wound film capacitors), wrap and fill capacitors, epoxy case capacitors, metal hermetically sealed capacitors, radial lead type capacitors, axial lead type capacitors, ceramic capacitors, disc capacitors, electrolytic type capacitors, etc. In a preferred embodiment, the present invention may be metalized and wound to create a wound film capacitor.

For example, the polycarbonate can be placed between two metal electrodes or plates to form a capacitor. The fluoromethyl polycarbonate material has a fast response with an electric field is applied and released which allows for an increase in ability of the capacitor to store and deliver electrical energy. The high dielectric strength allows for the fluoromethyl polycarbonate material of the present invention to function without experiencing a material failure under a significant electrical field. The high glass transition temperature enables the fluoromethyl polycarbonate to retain its other favorable properties at high working temperatures and also allows for workability in the manufacturing process.

Capacitors employing the fluorinated polycarbonates of the invention can be tailored to operate with high energy density and at high temperatures. For example, in an embodiment of the invention a capacitor employing a fluorinated polycarbonate of the invention has an energy density of about 8 J/cc or greater, preferably about 10 J/cc or greater, and more preferably 12 J/cc or greater. In an embodiment of the invention a capacitor employing a fluorinated polycarbonate of the invention can operate at temperatures of at least 140° C., preferably at least 150° C., more preferably at least 180° C.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Synthesis of Compounds

Synthesis of 4,4'(1,3-Difluoropropane-2,2-diyl)diphenol (diF BPA)

Phenol in the amount of 9.41 g was added to a 50 mL round bottom flask with a stir bar. The phenol was warmed until a homogenous solution was attained. Three drops of mercaptopropionic acid and 500 mg of amberlist 15 were added to the phenol solution. After purging the reaction system with nitrogen gas, 2.35 g difluoroaceton was added dropwise. Then the reaction was stirred for 3 days at room temperature. Reaction completion was confirmed by TLC. The product was extracted with 250 mL ethyl acetate, washed three times with 100 mL of water and washed one time with 150 mL of brine. The collected organic layers were combined and dried over sodium sulfate and concentrated under reduced pressure to produce the target crude compound. Further purification was achieved by flash chromatography (methylene chloride/acetone) on silica gel to produce the pure monomer as white crystals.

Example 1

Films of the compounds listed in Table 1 were synthesized and/or commercially obtained. The films were prepared for measurement by evaporating aluminum electrodes onto surfaces to form a parallel plate capacitor. Complex conductance measurements were then performed using a CGA-85 capacitance measuring assembly. The equivalent parallel capacitance, C, and conductance divided by the angular frequency, G/ω, were measured. Temperature was varied using two different systems. Some measurements were carried out in vacuum from 5.5 to 350 K in a Precision Cryogenics CT-14 dewar, and the temperature was controlled using a LakeShore Cryotronics DRC 82C temperature controller. Other measurements were carried out at atmospheric pressure in flowing nitrogen gas using a Novocontrol sample holder and Quatro temperature controller from 123 to 523 K. In both cases, the temperature was held constant for the duration of the experiment. In each case, the sample was equilibrated at each pressure for 30 min, decreasing from the highest pressure. The data were transformed to the complex relative permittivity as follows. Geometrical measurements were made and ε' was calculated at 1000 Hz and room temperature using the usual equation for a parallel plate capacitor $$\varepsilon' = \frac{Cd}{\varepsilon_0 A} \quad (1)$$

$\varepsilon_0$ is the permittivity of free space, A is the area of the electrodes, and d is the thickness of the sample. The real part of the relative permittivity was calculated at other temperatures, pressures, and frequencies by multiplying the ratio of the capacitances by 3.79. This procedure is based on the assumptions that thermal expansion is insignificant in the case of temperature variation and that isothermal bulk modulus is not important for reduction of the variable pressure data. Finally, the imaginary part of the relative permittivity, $\varepsilon''$, at all temperatures, pressures, and frequencies was calculated using $$\varepsilon'' = \varepsilon' \tan\delta = \varepsilon' \frac{G}{\omega C} \quad (2)$$

The $d_c$ dielectric strength was measured using a Hippotronics model HD140 Auto A, ac/dc hipot tester. The samples were immersed in a Fluorinert FC-770 high dielectric strength fluid to suppress surface events that were not indicative of the bulk dielectric properties. The sample was placed on a polished conducting steel ground plane. The upper electrode was a 1 cm diameter tool steel post ~75 mm in length. The weight of the post was used to establish a consistent contact pressure between the electrodes and the sample. The edge of the cylindrical electrode post was radiused in accordance with ASTM D3755 test procedure in order to minimize the probability of edge breakdown during testing. The face of the electrode was polished to a mirror finish with 0.1 μm polish compound to minimize the probability of a breakdown event being initiated by the surface texture of the electrode. A voltage ramp rate of 500 Vdc/s was used throughout the test. The Hippotronics hipot tester was set to trigger at a current of 1 mA for all tests. The applied voltage at breakdown was converted to an electric field using the measured sample thickness. The cumulative probability for failure was estimated using the median rank approximation. A Weibull two-parameter probability distribution $$P(E_b) = 1 - e^{-(Eb/E0)^{\alpha W}} \quad (3)$$

was fit to the experimental data. $P(E_b)$ is the cumulative probability of failure for a given electric field, $E_b$. $E_0$ is the dielectric strength. The exponent $\alpha W$ is a shape parameter that is related to the spread in observed values.

Table 1 illustrates the collected data for the given experimental conditions.

TABLE 1

| Material | $\varepsilon'$ (at 1 kHz) | $E_b$ (V/μm) | $T_g$ (° C.) | Gamma (° C.) | U (J/cm$^3$) | $E_{act}$ (kcal/mol) |
|---|---|---|---|---|---|---|
| BPA-PC | 2.96 | 631 | 157 | −93 | 5.22 | 11.25 |
| CN PC | 4.17 | 684 | 167 | −77 | 8.63 | 9.89 |
| CN(G)-PC | 4.38 | 796 | 177 | −33 | 12.28 | 15.13 |
| DiF BPA-PC | 4.18 | 779 | 134 | −83 | 11.22 | 9.80 |
| DiF TABPA-PC | 3.30 | 587 | 223 | −20.57 | 5.03 | 19.87 |

Thus, the data in Table 1 demonstrates the compositions of the invention having rotable fluoromethyl groups, such as DiF BPA-PC, provide better dielectric properties than that of polycarbonates of bisphenol A, those substituted with a nitrile group, or those substituted with fluorine on the benzene ring. Further, the dipole density and glass transition temperatures can be tailored by the selection of methyl substitution and selection of polymeric units forming the polymer backbone. The compounds of the invention possess fast relaxations of the fluoromethyl groups which represent a loss that contributes to high dielectric constants having low loss as room temperature when compared to existing polycarbonates. The data in Table 1 also demonstrates that the short-tethered nitrile exhibited better properties for dielectric materials than the long-tethered nitrile compounds previously studied. While not wishing to be bound by the theory, it is believed that the short-tethered nitrile did not exhibit the substantially similar properties as the DiF BPA-PC because the short-tether nitrile suffered from too much friction in rotation resulting in inadequate amount of energy released through dipole relaxation. All the materials in Table 1 other than BPA-PC show significant loss in the room temperature region of their respective spectra making them poor candidates for capacitor dielectrics. Except that DiF BPA-PC shows superior properties and enhanced dielectric properties over all materials in Table 1 including BPA-PC. While DiF BPA-PC does not have a glass transition temperature as may be desired for all end-uses, it can be copolymerized with polymers having high glass transition temperatures, such as high tetraaryl materials.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A composition comprising:
a monomer, analog, and/or derivative of Structure I

(Structure I)

wherein n is between 1 and 1000; wherein $R_1$ or $R_2$ are substitutions of the formula $C_xH_yF_z$ where x can be any number from 1 to 5, y can be any number from 1 to 8, and z can be any number from 1 to 3, and at least either $R_1$ or $R_2$ is fluorinated.

2. The composition of claim 1, wherein the monomer, analog, and/or derivative comprises an oligomer, polymer, copolymer, terpolymer, and/or analog of a)

3. The composition of claim 1 wherein the monomer, analog, and/or derivative forms a homopolymer, copolymer, and/or terpolymer.

4. The composition of claim 3, wherein the homopolymer, copolymer, and/or terpolymer is a resin, epoxy resin, polycarbonate, polyacrylate, polyester, poly ether, polysiloxane, polysulfide, and/or polysulfone.

5. The composition of claim 4, wherein the monomer, analog, and/or derivative forms a homopolymer, copolymer, and/or terpolymer in a polycarbonate.

6. The composition of claim 5, wherein the polycarbonate comprises an analog of Structure I.

7. The composition of claim 5, wherein the polycarbonate comprises a copolymer of Structure I.

8. The composition of claim 5, wherein the monomer, analog, and/or derivative is a copolymer of bisphenol A, tribisphenol A, tetraarylbisphenol A, and 4,4'-bisphenol, and/or analogs or derivatives of the same.

9. A dielectric composition comprising:
a polycarbonate of a homopolymer, copolymer, terpolymers, derivative and/or analog of the following formula wherein n is between 1 and 1000; wherein $R_1$ and $R_2$ are substitutions of the formula $C_xH_yF_z$ where x can be any number from 1 to 5, y can be any number from 1 to 8, and z can be any number from 1 to 3, and at least either $R_1$ or $R_2$ is fluorinated.

10. The composition of claim 9, wherein is a polycarbonate of a polymer, copolymer, terpolymer, or analog of a)

b)

c)

d)

11. The dielectric composition of claim 10, wherein the composition comprises a resin or film.

12. The dielectric composition of claim 10, wherein the composition has a glass transition temperature greater than 120° C.

13. The dielectric composition of claim 10, wherein the polycarbonate comprises a copolymer of bisphenol A, tri-bisphenol A, tetraarylbisphenol A, and 4,4'-bisphenol, and/or analogs or derivatives of the same.

14. A capacitor comprising:
the polycarbonate of claim 9.

15. The capacitor of claim 14, wherein the polycarbonate comprises a polymer, copolymer, terpolymer, or analog of a)

16. The capacitor of claim 15, wherein the capacitor is a dielectric capacitor, a variable capacitor, a film capacitor, a wrap and fill capacitor, an epoxy case capacitor, a metal hermetically sealed capacitor, a radial lead capacitor, an axial lead capacitor, a ceramic capacitor, a disc capacitor, or an electrolytic capacitor.

17. The capacitor of claim 15, wherein the capacitor is a wound film capacitor.

18. The capacitor of claim 15, wherein the capacitor can operate at temperatures of at least 140° C., and wherein the capacitor has an energy density of 8 J/cc or greater.

19. The capacitor of claim 15, wherein the polycarbonate comprises a copolymer of bisphenol A, tribisphenol A, tetraarylbisphenol A, and 4,4'-bisphenol, and/or analogs or derivatives of the same.

20. The capacitor of claim 15, wherein the capacitor has an energy density of 10 J/cc or greater, and can operate at temperatures of at least 150° C.

* * * * *